(12) United States Patent
Bengtson

(10) Patent No.: US 8,932,664 B2
(45) Date of Patent: Jan. 13, 2015

(54) SURGICAL FINGER, HAND AND ARM BARRIER COATING AND COVERING, METHOD AND SYSTEM

(71) Applicant: Bradley P Bengtson, Grand Rapids, MI (US)

(72) Inventor: Bradley P Bengtson, Grand Rapids, MI (US)

(*) Notice: Subject to any disclaimer, the term of this patent is extended or adjusted under 35 U.S.C. 154(b) by 0 days.

(21) Appl. No.: 13/651,729

(22) Filed: Oct. 15, 2012

(65) Prior Publication Data

US 2013/0095227 A1 Apr. 18, 2013

Related U.S. Application Data

(60) Provisional application No. 61/546,741, filed on Oct. 13, 2011.

(51) Int. Cl.
| | | |
|---|---|---|
| *A41D 1/00* | (2006.01) | |
| *A41D 19/00* | (2006.01) | |
| *B05D 3/02* | (2006.01) | |
| *B05D 5/00* | (2006.01) | |
| *A61B 19/04* | (2006.01) | |
| *B29C 41/00* | (2006.01) | |
| *B29D 99/00* | (2010.01) | |
| *A61B 17/00* | (2006.01) | |
| *B05D 1/18* | (2006.01) | |

(52) U.S. Cl.
CPC . *B05D 5/00* (2013.01); *A61B 19/04* (2013.01); *B29C 41/00* (2013.01); *B29D 99/0067* (2013.01); *A61B 2017/00526* (2013.01); *A61B 2017/00889* (2013.01); *A61B 2017/00893* (2013.01); *A61B 2019/043* (2013.01); *B05D 1/18* (2013.01)
USPC ............ 427/2.3; 427/430.1; 427/2.1; 223/78

(58) Field of Classification Search
USPC ................................................. 427/2.3; 223/78
See application file for complete search history.

(56) References Cited

U.S. PATENT DOCUMENTS

| | | | | |
|---|---|---|---|---|
| 5,041,287 | A * | 8/1991 | Driggers et al. | 424/78.35 |
| 6,139,856 | A * | 10/2000 | Kaminska et al. | 424/404 |
| 6,337,076 | B1 * | 1/2002 | Studin | 424/401 |

* cited by examiner

*Primary Examiner* — Cachet Sellman
(74) *Attorney, Agent, or Firm* — Ryan Krumholz & Manion, S.C.

(57) ABSTRACT

A protective coating solution, liquid, gel, or film and a method of using such a material to provide a sterile covering for fingers, hands, arms or other selected skin surface for use as a glove substitute.

9 Claims, 7 Drawing Sheets

SURGICAL FINGER, HAND AND ARM BARRIER COATING AND COVERING, METHOD AND SYSTEM

RELATED APPLICATIONS

This application claims the benefit of co-pending provisional patent application Ser. No. 61/546,741 filed 13 Oct. 2011.

BACKGROUND OF THE INVENTION

The present invention relates to a sterile covering or barrier protective liquid, gel, material or film and, more particularly to a method of using such a material to create a sterile covering for fingers, hands, arms or other selected skin surface to act as glove substitute.

During surgery and other medical procedures sterility is essential to prevent contamination and the spread of diseases, bacteria and viruses. Likewise, it is also essential that hand coverings do not limit the surgeon's or medical personnel's feel and touch, e.g. tactile sensation, when performing a medical procedure or examination. In addition, areas like the food industry, salon services, dentistry and a wide variety of other manufacturing and specialty services require protection for themselves and their patients or clients.

Most commonly, surgical gloves, e.g. latex gloves and non latex polymers, are standard and used during surgery and other procedures. However, the use of surgical gloves may be a cumbersome process when putting on and removing the gloves, creates a great deal of solid waste and may be overkill for certain smaller procedures. They also create a tactile barrier to the sensitivity or the surgeon or person wearing the gloves. While there have been improvements in the strength and thinness of these gloves, they nonetheless tend to be thicker than desired, adding to diminished tactile feeling of the surgeon or medical personnel. There is also increasing medical evidence to show that most patient infections originate from the patient's own skin verses the surgeon's skin. Therefore protection is needed for both the operator and the patient or client.

Artificial skins have been developed that are used to treat sores and wounds on a patient. Such artificial skins may be sprayed onto the skin or applied topically to particular areas of the skin. However, such artificial skins are not well adapted for surgical uses, as they do not necessarily hold up and are not durable enough to a function in a surgical environment. Further, they do not provide for an adequate barrier of protection, and in addition may not prevent bacteria from growing on the surface as a biofilm.

SUMMARY OF THE INVENTION

The present invention provides a surgical finger, hand, or arm barrier covering and a method and system of applying the covering. The hand covering provides a durable barrier between medical personnel and a patient during a surgical procedure or examination and also with other nonmedical uses as described above. The hand covering is resistant to dissolution when in contact with bodily fluids or water so that it will retain its protective barrier during the particular medical procedures or examinations, would bind any residual bacteria into the follicles or skin, and create a sterile surface over the fingers or hands circumferentially creating a sterile barrier. In addition, and as a completely different application, the material may also be used as a skin prep application or sealant after the skin prep and applied directly over the skin were an incision is to be made or to cover areas such as the nipple to prevent any bacteria coming from out of the ducts and onto the skin surface or into the wound.

The present further invention contemplates a method of providing the fingers, hands, or arms with a covering for use during a surgical procedure, and a method of providing a finger covering or a sterile covering for the fingertips only. The process includes dipping the user or medical personnel's fingers or hands in a solution, or suspension of material, removing the hands, and allowing the solution to dry, thereby forming the surgical hand covering. Once the medical procedure is finished, the fingers or hands may be washed in a solution or solvent that will remove the surgical hand covering, if needed. As an alternative, the solution or suspension may be applied to the hands and rubbed in evenly to provide uniform coverage.

The present invention further contemplates a finger dip apparatus for retention of the solution or suspension, and into which the fingers may be dipped for application. A larger apparatus may also be used to accommodate the entire hand, entire arm, or other larger body area for uniform application of the suspension.

Alternatively, a sprayer system may be utilized to spray and or dispense the material. After application of the suspension by the sprayer, the covering would be allowed to air dry or may be placed into a air blower or dryer to be dried more quickly.

In another embodiment, the coating is applied as an extremely thin film to the fingers, hands or arms and peeled off for removal, or removed with a solvent.

The specific material to be used as a coating may be a single agent such as a silicone or other plastic polymer or a may be combination of materials including antiseptics such as those marketed under the names CHLORAPREP®, HIBICLENS®, BETADINE®. Other alcohols and antibiotics that may further suppress bacteria may be used in combination with other materials such as flexible Collodion, ether free Collodion, cyanoacrylates such as those used in SUPER GLUE®, and DERMABOND® materials. Any of these combinations may also be applied as a thin film or plastic polymer.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention which is defined by the claims.

Figure 1A:
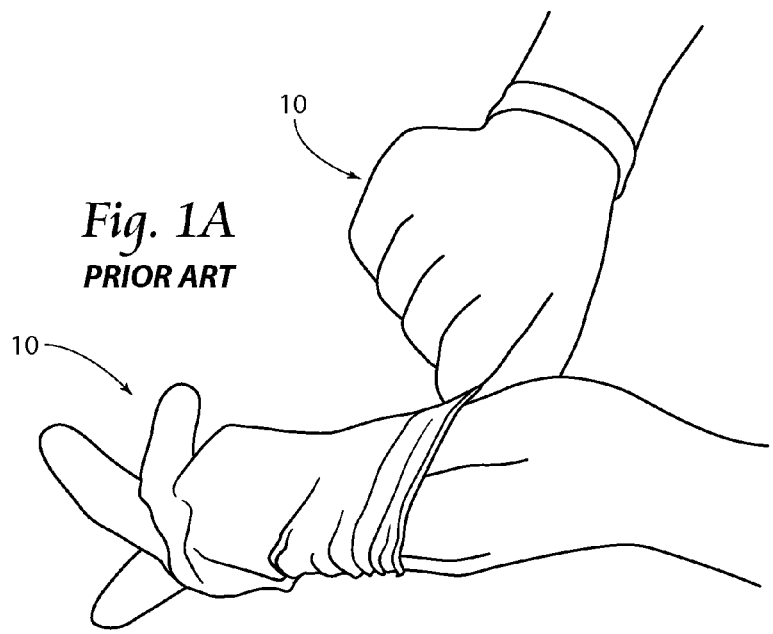
FIG. 1A depicts the process of applying prior art gloves for use in a medical procedure.
Figure 1B:
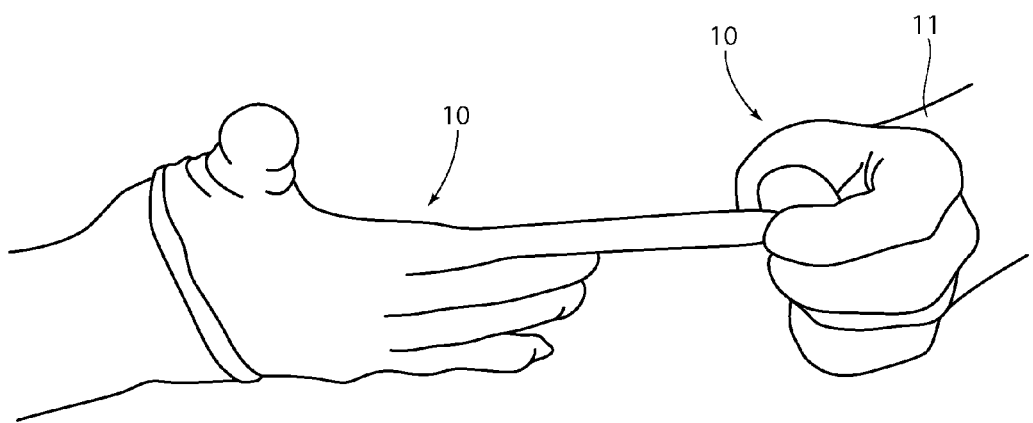
FIG. 1B depicts the gloves of FIG. 1A being removed after use in medical procedure.

FIGS. 1A and 1B demonstrate prior art gloves 10 for use in surgical procedures. In FIG. 1A, the gloves 10 are being applied prior to a surgical or medical procedure. The surgeon or other medical personnel will pull the gloves 10 over their hands 11 and adjust them so that they fit properly on the user's hands 11. The gloves 10 are normally made from a thin silicone, latex or rubber material, e.g. latex, that allow the gloves 10 to be flexible enough so that the user can adjust them for proper fit. Because the gloves 10 are mass produced, the gloves 10 may not adequately fit the user's hands, either being too tight and not properly conforming to the specific user's hands, or they may be too loose, which can result in the gloves 10 being a hindrance during a surgical procedure. If the gloves 10 are too tight, the gloves 10 may also rip when being put on, thereby causing the person to have to remove the gloves, throw them away, and put on a new set of gloves. In addition the glove thickness decreases the tactile sensation or the wearer and also creates and adds to the great medical waste burden.

FIG. 1B demonstrates the gloves 10 being removed from the user's hands 11. Removal may be a tedious process, particularly if the gloves 10 tightly fit the user's hands. This is also true because the material of the gloves 10 must also be sufficiently strong to resist tearing and rips that may occur during use.

As previously noted, the materials used for these gloves 10 are rubber materials such as latex, or other materials with similar properties. Though the gloves 10 are designed to be thin, they must be sufficiently strong, e.g. thick, so that they will not fail during use, often diminishing or lessening the tactile feel of the user.

The present invention provides an alternative to gloves 10. The present invention comprises a surgical hand covering that may be applied to the user's fingers in particular and or the hands in general, or may be used to cover any other skin surface. The hand covering will be used in lieu of gloves 10 being put on the user's hands.

Figure 2:
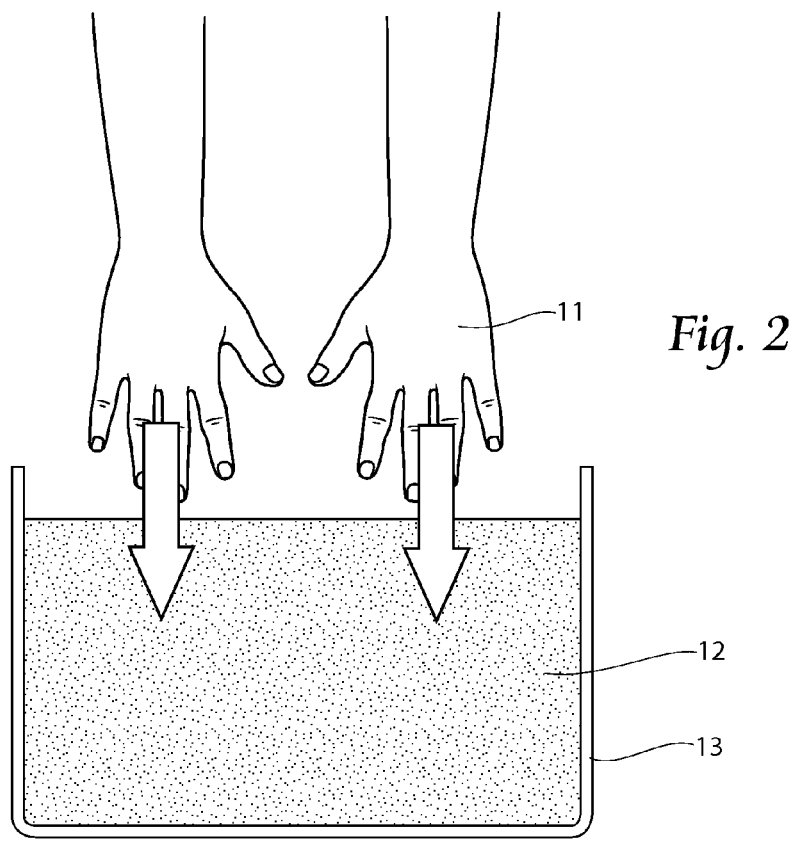
FIG. 2 demonstrates a first step for applying a surgical finger or hand coating according to the present invention.

FIG. 2 shows the user's hands 11 prior being covered with the surgical hand covering of the present invention. The user's hands 11 will be washed and sterilized, as is typically done before surgical or medical procedures. A container 13 holding a coating solution 12 is made available to receive the user's hands 11. The user's hands will be sufficiently dry such that when they are put into the coating solution 12, the coating solution 12 will sufficiently adhere to the selected skin surface, such as the hands 11 shown in these views.

Figure 3:
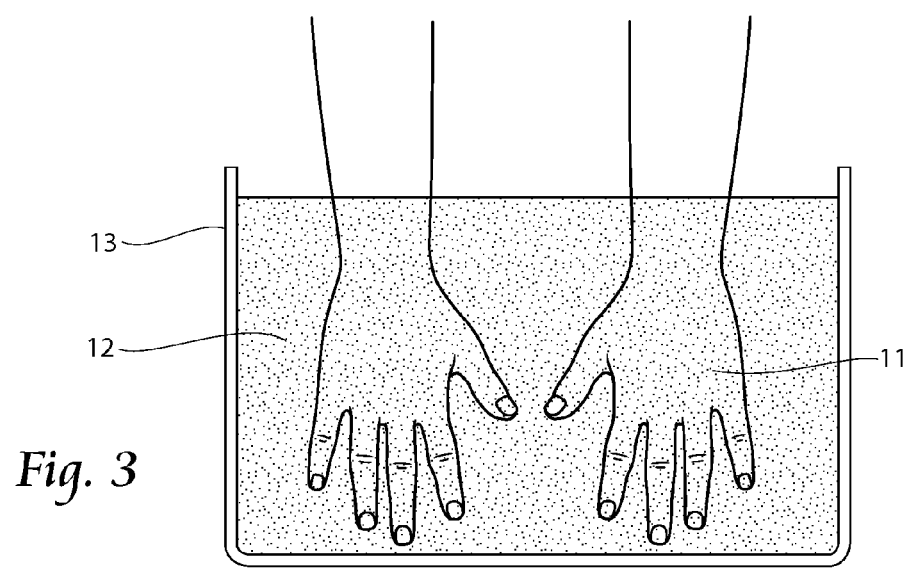
FIG. 3 provides a subsequent step for applying a surgical fingers or hand coating according to the present invention, with the hands being submersed into a solution containing the surgical hand covering material.

As is shown in FIG. 3, the user dips a selected skin surface, such as hands 11, into the container 13 so that the hands 11 are covered by the solution 12. The user will keep them within the solution 12 for a sufficient period of time necessary to coat the hands 11. The immersion time may be determined by the user. For example, the user may immerse just finger tips into the solution 12 for a quick, simple procedure, e.g. an office check-up, or may immerse the entire hand or arm for use in a more intricate or involved procedure, as for example, a surgical operation. As such, the present invention provides a hand covering that may be tailored particularly to the needs of a specific user and a specific procedure.

Figure 4:
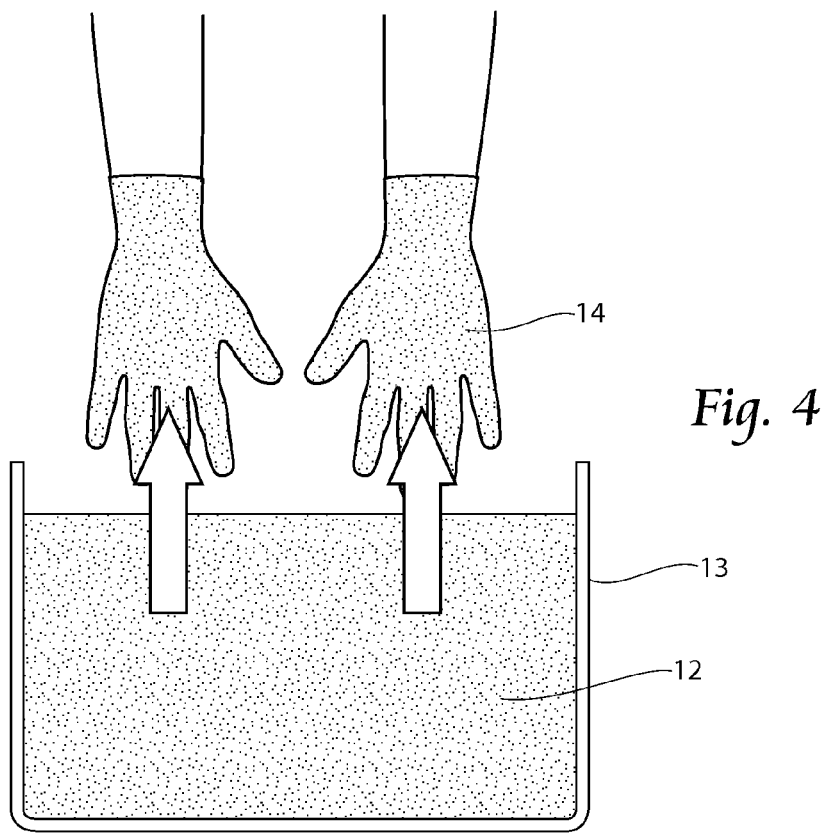
FIG. 4 provides a further step for applying a surgical finger or hand coating according to the present invention, with the hand being removed from the solution and allowed to dry.

With attention now to FIG. 4, it may be seen that once the hands 11 are sufficiently coated by the solution 12, the user will remove the hands 11 from the solution 12. Any excess coating solution 12 may be removed from the user's hands, if desired, by allowing the excess solution 12 to drip off. The hands 11 are preferably allowed to dry for a predetermined time prior to the performance of the medical or surgical procedure, whereby the surgical hand coating 14 of the present invention is formed. The coating solution 12 is preferably a quick drying solution to insure the hand coating 14 provides the necessary barrier against contamination prior to performing the particular procedure or operation. The step of dipping the hands into the solution 12 may be repeated if additional thickness is required.

Figure 5:
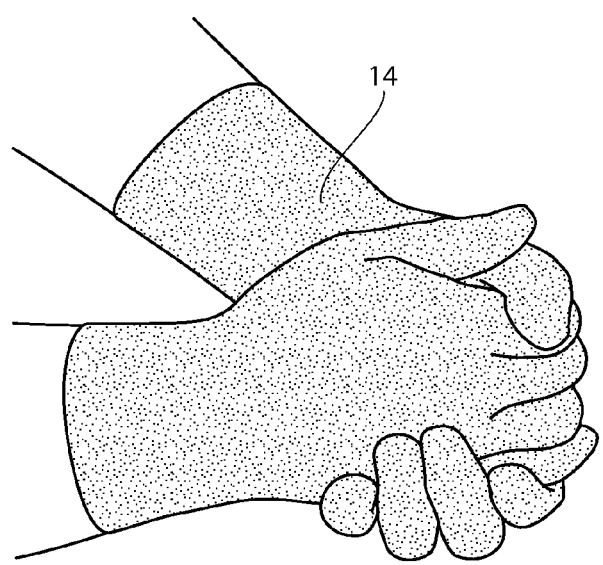
FIG. 5 provides an alternate step for the present solution wherein the hands are rubbed together after being removed from the hand covering solution.

FIG. 5 provides a further step of the method of the present invention. After the user has removed his hands as shown in FIG. 4, the user may rub his hands together so that the coating solution 12 will be evenly distributed and worked into all portions of the skin, thereby further increasing the hygienic barrier formed by the coating solution 12.

Figure 6:
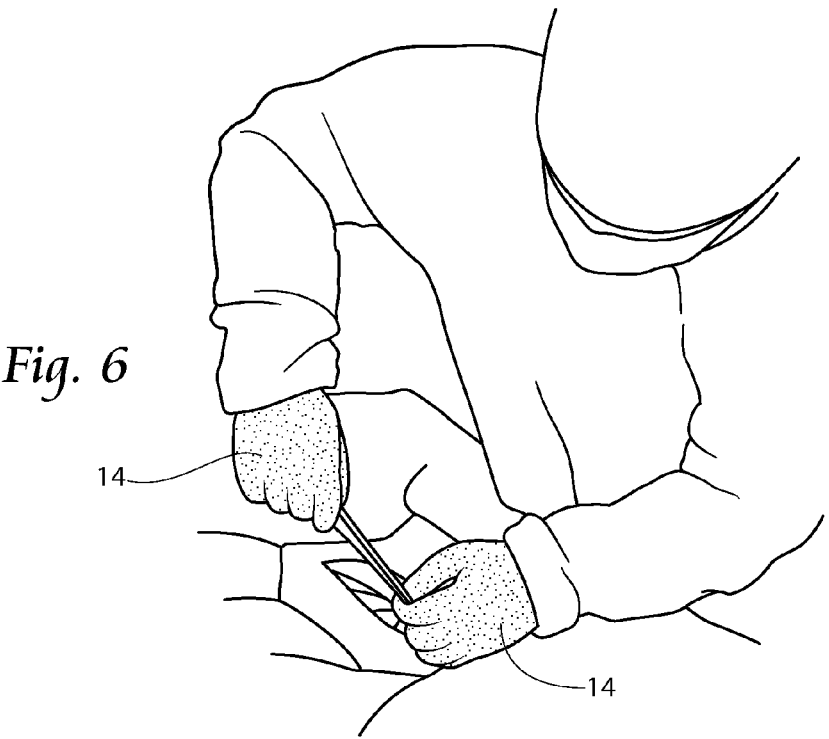
FIG. 6 depicts a user, such as a surgeon, performing a medical procedure while using the surgical hand coating of the present invention.

As shown in FIG. 6, the user is able to perform the medical procedure, without the need for gloves 10. The surgical hand coating 14 provides a sterile barrier that sufficiently prevents the transmission of unwanted materials, e.g. bacteria, in the same manner as for the prior art gloves. Further, the surgical hand coating 14 is thinner than the gloves 10 and directly follows the contours of the individual user's hands, which increases the tactile feel of the user. The result is that the user has better and more precise feel when carrying out a procedure.

Figure 7:
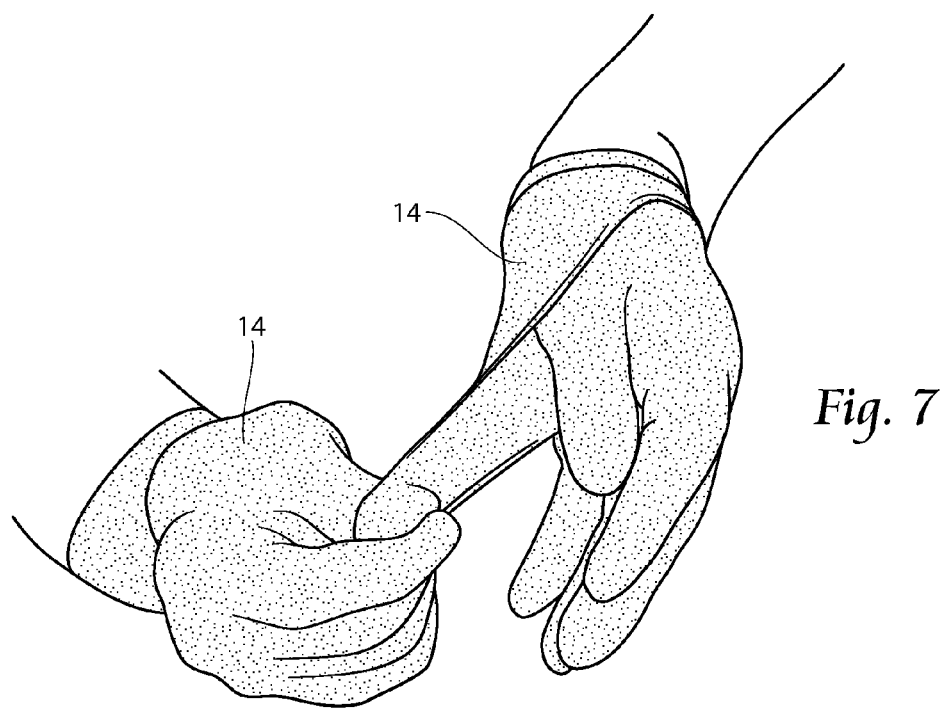
FIG. 7 depicts a surgeon removing the surgical finger or hand coating after surgery.
Figure 8:
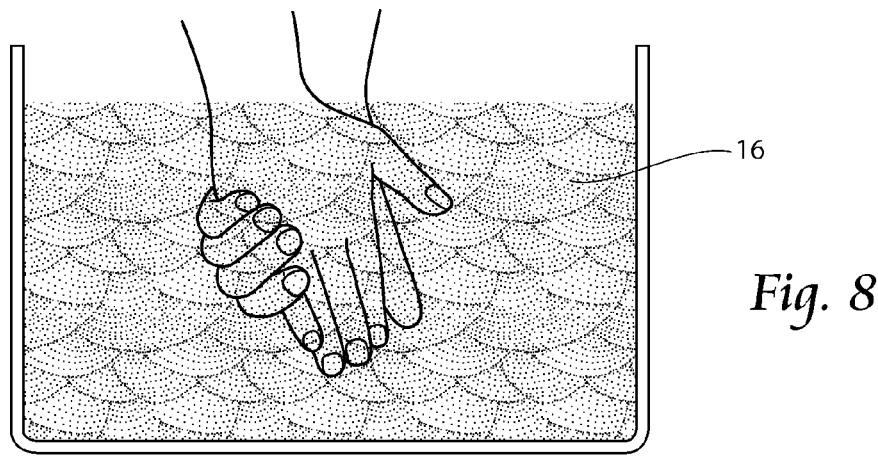
FIG. 8 demonstrates a user, such as a surgeon, removing any remaining surgical hand coating by washing the hands in a rinse solution.

Once the surgical procedure is completed, the surgical hand coating 14 may be peeled away from the user's hands, as is shown in FIG. 7. Any remaining surgical hand coating 14 may be further washed away in a solvent 16 particular to the composition of the coating solution 12, as is shown in FIG. 8. Alternatively, the coating solution 12 may be simply washed away without first peeling away the coating 14.

Figure 9:
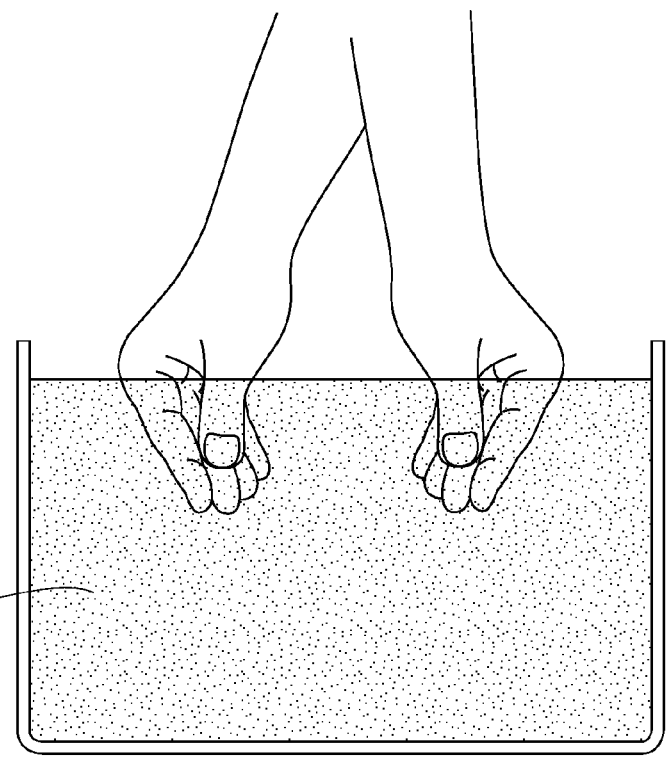
FIG. 9 depicts an alternate first step in the process of the present invention, wherein only the fingers are immersed in the solution containing the surgical hand covering material.
Figure 10:
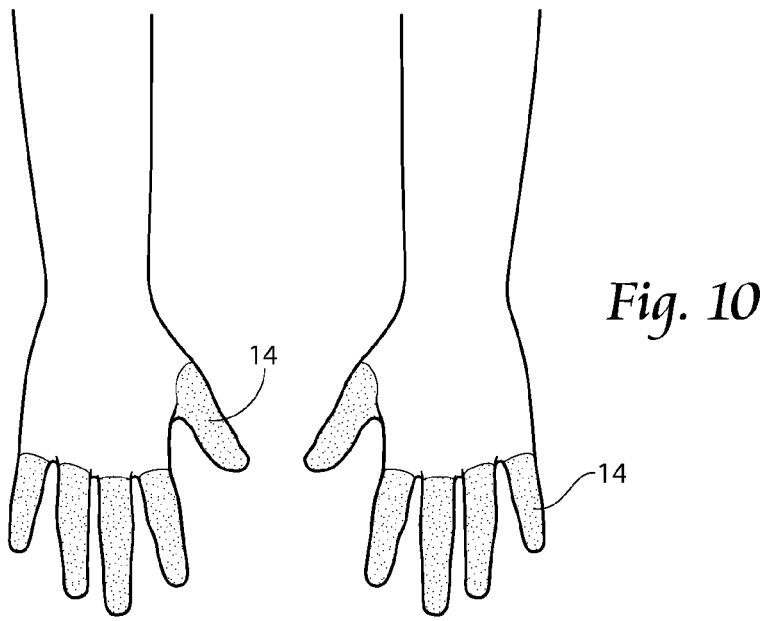
FIG. 10 depicts the fingers of FIG. 9 being removed from the solution and allowed to dry.

The surgical hand coating 14 of the present invention and the methods of forming the surgical hand coating 14 also allow for hand coatings 14 to be directed towards particular body parts, e.g. the user's fingers. As shown in FIG. 9, the user may dip only the fingers into the coating solution 12. The fingers are removed and allowed to dry, as shown in FIG. 10, in the similar fashion as described previously with respect to the coating for the entire hand.

Figure 11:
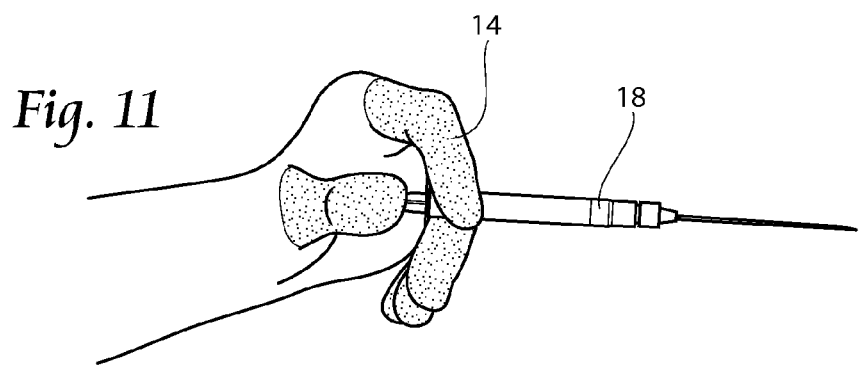
FIG. 11 demonstrates the use of a syringe after application of the hand solution as shown in FIG. 10.

The ability to isolate the surgical hand coating 14 to a particular skin surface reduces waste and costs associated with prior art hand coverings 10. For example, as shown in FIG. 11, the user may apply the coating only to the fingers, which thereby provides a sufficient barrier for certain routine procedures, such as delivering or injecting a medication with a syringe 18. Since it is not necessary to sterilize the entire hand for such a procedure, use of the present coating 14 on the fingers only, relieves the user of the unnecessary time and effort required to apply full gloves 10 on the hand. Thus, the procedure is made more efficient than use of the prior art gloves 10, while also being more cost effective.

In addition to providing a better fit than prior art gloves 10 and other known hand coverings, the present invention also allows the user to be more responsive to potential problems during a medical procedure. For example, because tactility is improved with the present invention, the user is more able to realize if an instrument pierces through the surgical coating 14. This minimizes the possibility that contamination is transmitted through open wounds. In the same fashion, the surgical coating solution 12 may include skin color changing agents that react when the surgical coating 14 is pierced, thereby warning the user if the surgical coating 14 is compromised. For example, the surgical coating 14 may change color when pierced by a surgical instrument. Surgical gloves sold under the BIOGEL PI INDICATOR® System name may be seen as an example of such a feature.

Figure 12:
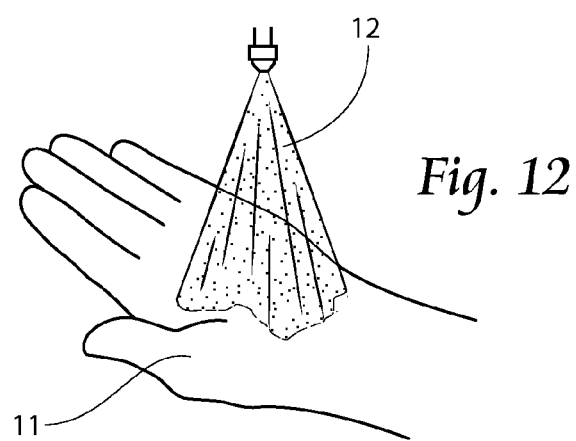
FIG. 12 depicts an alternative first step for applying the material as a spray that is sterilely sprayed on to the user's selected skin surface and allowed to dry or rubbed into the hands or arms.
Figure 13:
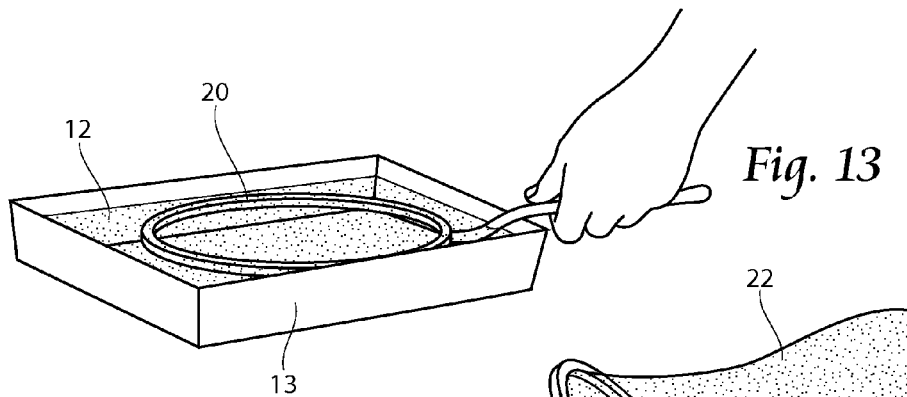
FIG. 13 depicts an alternative first step for applying the material, and showing a hoop device inserted into a vessel containing the material.
Figure 14:
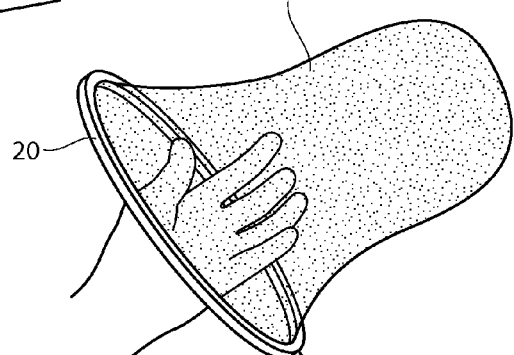
FIG. 14 depicts a subsequent step for the method depicted in FIG. 13, in which the hoop device retains a film of material and the user inserts a selected skin surface, seen as a hand in this view, into the film.

As seen in FIGS. 12-16, alternative methods of applying the coating solution 12 to a selected skin surface may be envisioned. For example, and as seen in FIG. 12, the solution 12 may be applied by spraying. FIGS. 13 and 14, illustrate the solution 12 applied by way of a hoop device 20 inserted into a container 13 holding the solution 12. As further seen in FIG. 14, the hoop device 20 forms and retains a film 22 of solution 12 while the user inserts a selected skin surface, seen as a hand 11 in this view, into the film 22.

Figure 15:
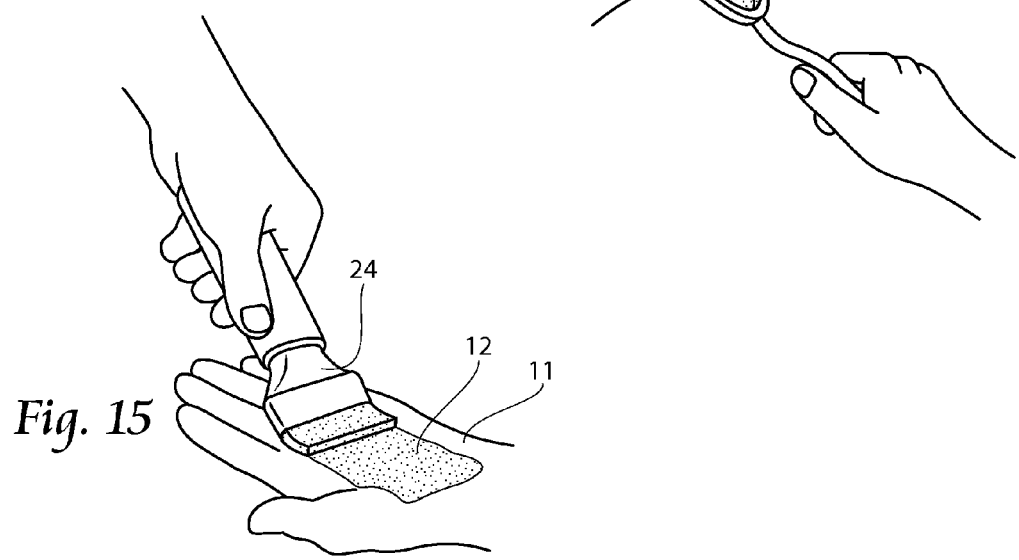
FIG. 15 depicts another alternative first step for applying the material, and showing an applicator device transferring the material to a selected skin surface.

The novel solution 12 may also be applied to the skin as a surgical prep solution that will also bind any bacteria to create a biofilm into the skin thereby decreasing contamination. The view of FIG. 15 illustrates a first step for applying the solution 12 in this manner, and shows an applicator device 24 transferring the solution 12 to a selected skin surface, seen as a hand 11.

Figure 16:
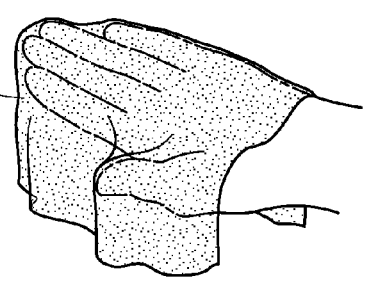
FIG. 16 depicts another alternative first step for applying the material, and showing a thin film of the material draped over a selected skin surface.

Yet another method for applying the solution 12 to a selected skin portion may be seen in FIG. 16. In this view, the solution 12 is illustrated as a film 22 that may be draped over the hand 11, or other skin surface.

The present invention may be formulated from any material that will provide the necessary protective coating while providing an improved tactile feeling as compared to prior art gloves. For example the material may be a silicone polymer or a combination of silicone, and other materials such as an antiseptic, antimicrobial, antibiotic, or other skin sealants such as collodion or cyanoacrylates. Other examples of acceptable coating materials include polymers, such as a polyester material, a PEG material, a polyvinyl material, a nylon material, synthetic rubber, a polypropylene material, or other material that is capable of forming a surgical hand coating 14 and that will form the necessary artificial barrier according to the present invention. The material will allow for a surgical hand coating 14 that is flexible when applied to the user's hands so as to not crack, break, or rupture during a surgical procedure, examination or other manual uses. The material will also be thin enough when dried so that the user will have increased feel when compared to prior art gloves. As mentioned, the specific material to be used as a coating may be a single agent such as a silicone or other plastic polymer or a may be combination of materials including antiseptics such as those marketed under the names CHLORAPREP®, HIBICLENS®, BETADINE®. Other alcohols and antibiotics that may further suppress bacteria may be used in combination with other materials such as flexible Collodion, ether free Collodion, cyanoacrylates such as those used in SUPER GLUE®, and DERMABOND® materials. Any of these combinations may also be applied as a thin film or plastic polymer.

The prior art does not provide a method wherein a surgical coating is provided that will provide a barrier against bacteria and other contaminants, without the requirement of an external glove or other materials to be used in concert with the surgical hand coating 14. Prior art gloves 10 are pre fit and preformed versus the present invention of an application of a solution or suspension that is allowed to bind to the skin and provide a custom fit physical barrier to the transgressions of bacterial or contamination and will protect both the patient or the client as well as the physician, surgeon or user.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

The invention claimed is:

1. A method of coating a predetermined skin surface with a protective coating including the steps of:
   providing a coating solution;
   selecting a predetermined skin surface for application of said coating solution;
   applying said coating solution to said skin surface comprising the steps of:
       providing a hoop device;
       inserting said hoop device into a container of said solution;
       collecting a film of said solution on said hoop device; and
       applying said film to said predetermined surface; and
   drying said coating solution.

2. The method of claim 1 wherein said predetermined skin surface comprises at least one hand.

3. The method of claim 1 wherein said predetermined skin surface comprises at least one finger portion.

4. The method of claim 1 wherein said solution comprises a polymer.

5. The method of claim 1 wherein said solution comprises a silicone.

6. The method of claim 4 wherein said solution further includes an antiseptic.

7. The method of claim 5 wherein said solution further includes an antiseptic.

8. The method of claim 1 wherein said solution is a collodion.

9. The method of claim 8 wherein said solution further includes an antiseptic.

* * * * *

UNITED STATES PATENT AND TRADEMARK OFFICE
CERTIFICATE OF CORRECTION

| | | |
|---|---|---|
| PATENT NO. | : 8,932,664 B2 | Page 1 of 1 |
| APPLICATION NO. | : 13/651729 | |
| DATED | : January 13, 2015 | |
| INVENTOR(S) | : Bradley P. Bengtson | |

It is certified that error appears in the above-identified patent and that said Letters Patent is hereby corrected as shown below:

Title page, item (74) Attorney, Agent, or Firm -- Delete "Ryan Krumholz & Manion, S.C." and insert
    -- Ryan Kromholz & Manion, S.C. --

Signed and Sealed this
Twenty-third Day of June, 2015

Michelle K. Lee
*Director of the United States Patent and Trademark Office*